US00RE50250E

(19) United States
(12) Reissued Patent
Jacoby et al.

(10) Patent Number: US RE50,250 E
(45) Date of Reissued Patent: Dec. 31, 2024

(54) PROCESS FOR THE PREPARATION OF CIS-ALPHA,BETA SUBSTITUTED CYCLOPENTANONES

(71) Applicant: FIRMENICH SA, Satigny (CH)

(72) Inventors: Denis Jacoby, Satigny (CH); Lucia Bonomo, Satigny (CH)

(73) Assignee: FIRMENICH SA, Satigny (CH)

(21) Appl. No.: 17/866,170

(22) Filed: Jul. 15, 2022

Related U.S. Patent Documents

Reissue of:
(64) Patent No.: 11,339,113
Issued: May 24, 2022
Appl. No.: 17/273,357
PCT Filed: Dec. 16, 2019
PCT No.: PCT/EP2019/085416
§ 371 (c)(1),
(2) Date: Mar. 4, 2021
PCT Pub. No.: WO2020/127094
PCT Pub. Date: Jun. 25, 2020

(30) Foreign Application Priority Data

Dec. 19, 2018 (EP) ..... 18214113

(51) Int. Cl.
*C07C 67/327* (2006.01)
*C07C 69/716* (2006.01)

(52) U.S. Cl.
CPC ..... *C07C 67/327* (2013.01); *C07C 69/716* (2013.01); *C07C 2601/08* (2017.05)

(58) Field of Classification Search
CPC . C07C 67/327; C07C 69/716; C07C 2601/08; C07C 67/54; C07C 67/31; C07C 67/313; C07C 69/708
See application file for complete search history.

(56) References Cited

U.S. PATENT DOCUMENTS 5,728,866 A 3/1998 Rautenstrauch et al.
7,271,296 B2 9/2007 Ernst et al.

FOREIGN PATENT DOCUMENTS

EP 1900720 A1 * 3/2008 ..... C07C 69/738
GB 1353574 * 5/1974
GB 1353574 A 5/1974
GB 1438479 A 6/1976
JP H0363247 A 3/1991
JP 2002069477 A 3/2002
JP 2007512235 A * 5/2007
JP 2015177742 A 10/2015

OTHER PUBLICATIONS

International Search Report and Written Opinion for corresponding PCT/EP2019/085416 mailed Mar. 6, 2020, 10 Pages.
Mori et al., "Synthesis of Enantiomerically Pure (10R, 11S)-(+)-Juvenile Hormones I and II", Tetrahedron, 1988, pp. 343-354, 44(2).
Zhao et al., "Study on the condensation of cyclohexanone with glycerol using different solid acid catalysts", Applied Chemical Industry, 2008, pp. 865-882, 37(8).
Seto et al., "Purification and cDNA cloning of a wound inducible glucosyltransferase active toward 12-hydroxy jasmonic acid", Phytochemistry, 2009, pp. 370-379, 70.
Kametani et al. (Efficient Chiral Synthesis of Melillo's Lactone, a Key Intermediate for the Synthesis of Thienamycin, J. Chem Soc., Chem. Cummun., pp. 646-647, Published 1989) (Year: 1989).*
Krause N et al, "Synthesis of ( )-Methyl Epijasmonate and ( )-Methyl Dihydroepijasmonate by Diastereoselective Protonation", Oct. 1, 2001 (Oct. 1, 2001), vol. 2001, No. 20, p. 3837-3841.

* cited by examiner

*Primary Examiner* — Alan D Diamond
(74) *Attorney, Agent, or Firm* — Armstrong Teasdale LLP

(57) ABSTRACT

Described herein is a process for the preparation of a mixture of compounds of formula (I)

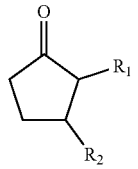

having a weight ratio of the cis-diastereomers to trans-diastereoisomers higher than 1:1, where $R_1$ represents a $C_{1-8}$ alkyl group, a $C_{2-8}$ alkenyl group or a $C_{2-8}$ alkynyl group, each optionally substituted with one or two of a $C_{1-4}$ alkyl alkoxy ether group and/or a $C_{1-4}$ alkyl carboxylester group and $R_2$ represents a $C_{1-6}$ alkyl, a $C_{2-6}$ alkenyl or a $C_{2-6}$ alkynyl group, each optionally substituted with a $C_{1-4}$ alkyl alkoxy ether group, a carboxylic acid group or a $C_{1-4}$ alkyl carboxylester group and compounds suitable in the process.

18 Claims, No Drawings

PROCESS FOR THE PREPARATION OF CIS-ALPHA,BETA SUBSTITUTED CYCLOPENTANONES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is *a reissue application of U.S. Pat. No. 11,339,113 B2, which was filed as U.S. patent application Ser. No. 17/273,357 on Mar. 4, 2021, and issued on May 24, 2022, which was filed as* a U.S. National Phase Application of International Patent Application No. PCT/EP2019/085416, filed Dec. 16, 2019, which claims the benefit of priority to European Patent Application No. 18214113.5, filed Dec. 19, 2018, the entire contents of which are hereby incorporated by reference herein.

TECHNICAL FIELD

The present invention relates to the field of organic synthesis. More particularly, it provides a process for the preparation of a mixture of compounds of formula (I) having a weight ratio of the cis-diastereomers to trans-diastereomers higher than 1:1 and compounds suitable in said process.

BACKGROUND

The compounds of formula (I), as defined in more detail below, can be generally useful as perfuming ingredients or as building blocks in the perfumery industry. The mixtures of cis-diastereomers and trans-diastereomers of compounds of formula (I) can also have certain beneficial olfactive effects.

The methods of preparation of said compounds and mixtures of said compounds reported in the prior art, such as in U.S. Pat. No. 5,728,866, EP1900720 or Eur. J. Org. Chem. 2001, 3837, are generally long and expensive. It is therefore highly desirable to access said compounds and mixtures of said compounds by using a simple and efficient process of preparation wherein the starting material is an easily accessible material.

To the best of our knowledge, the prior art did not disclose or suggest the process of preparation according to the present invention providing a direct access to compounds or mixtures of compounds of formula (I).

DESCRIPTION OF THE INVENTION

In order to solve the aforementioned problem, the present invention provides a process for the preparation of a mixture of compounds of formula (I)

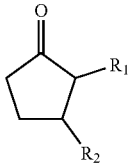

having a weight ratio of the cis-diastereomers to trans-diastereomers higher than 1:1, wherein $R_1$ represents a $C_{1-8}$ alkyl group, a $C_{2-8}$ alkenyl group or a $C_{2-8}$ alkynyl group, each optionally substituted with one or two of a $C_{1-4}$ alkyl alkoxy ether group and/or $C_{1-4}$ alkyl carboxylester group, and $R_2$ represents a $C_{1-6}$ alkyl group, a $C_{2-6}$ alkenyl group or a $C_{2-6}$ alkynyl group, each optionally substituted with an $C_{1-4}$ alkyl alkoxy ether group, a carboxylic acid group or a $C_{1-4}$ alkyl carboxylester group, by subjecting a mixture comprising compounds of formula (I)

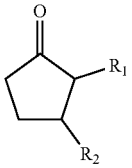

having a weight ratio of the cis-diastereomers to trans-diastereomers equal or lower than 1:1, wherein $R_1$ and $R_2$ have the same meaning as indicated above, to the steps comprising (a) ketal formation, (b) separating the trans-diastereomers and cis-diastereomers and (c) hydrolyzing the ketal of the cis-diastereomers.

By the terms "cis-diastereomer" and "trans-diastereomer", it is understood the normal meaning of said terms to the person skilled in the art. In the context of the present invention, the terms "cis-diastereomer" and "trans-diastereomer" mean the relative configuration of the substituent $R_1$ to the substituent $R_2$. The term "cis-diastereomer" means that the substituents $R_1$ and $R_2$ are sterically directed in the same direction relative to the cyclopentane ring whereas the term "trans-diastereomer" means that the substitutents $R_1$ and $R_2$ are sterically directed in different directions relative to the cyclopentane ring. Thus, the compounds of formula (I) comprise two cis-diastereomers having the absolute configuration according to formula (II)

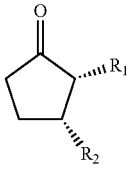

and (III)

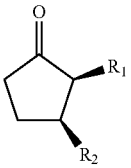

and two trans-diastereomers having the absolute configuration according to formula (III)

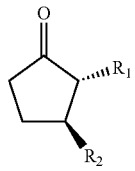

and (IV)

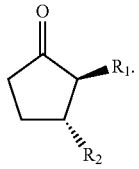

By the expression "weight ratio of the cis-diastereomers to trans-diastereomers higher than 1:1" of the prepared mixture, it is understood that the prepared mixture comprises more than 50% by weight of cis-diastereomers in comparison to less than 50% by weight of trans-diastereomers. According to a preferred embodiment, the weight ratio of cis-diastereomers to trans-diastereomers of the prepared mixture is at least 60:40, more preferably at least 70:30, more preferably at least 80:20 and even more preferably at least 85:15.

The weight ratio of the cis-diastereomers to trans-diastereomers can be determined by GC. Typically, the peaks of the corresponding cis-diastereomers or trans-diastereomers are determined by GC and the corresponding peak area is integrated and compared with each other.

By the terms "alkyl", "alkenyl" and "alkynyl", it is understood the normal meaning of the terms to the person skilled in the art. Alkyl, alkenyl and alkynyl are understood as comprising linear and branched alkyl, alkenyl or alkynyl groups. The term "alkenyl" is understood as comprising 1, 2 or 3 olefinic double bonds, preferably 1 olefinic double bonds. The term "alkynyl" is understood as comprising 1, 2 or 3 triple bonds, preferably 1 olefinic double bonds.

By the terms "$C_{1-4}$ alkyl alkoxy ether group", "carboxylic acid group" or "$C_{1-4}$ alkyl carboxylester group", it is understood the normal meaning of the terms to the person skilled in the art. $C_{1-4}$ alkyl alkoxy ether group is understood as a substituent being a $C_{1-4}$ alkyl group substituted with a $C_{1-4}$ alkoxy group. $C_{1-4}$ alkyl carboxylester group is understood as a substituent being a carboxyl group with a $C_{1-4}$ alkyl ester group; i.e. a COOR group wherein R may represent a $C_{1-4}$ alkyl group.

According to any embodiments of the invention, the compound of formula (I) is defined in that $R_1$ represents a linear $C_{3-7}$ alkyl group or a linear $C_{3-7}$ alkenyl group or a linear $C_{3-7}$ alkynyl group, preferably a linear $C_{4-6}$ alkyl group or a linear $C_{4-6}$ alkenyl group, even more preferably a linear $C_5$ alkyl group or a linear $C_5$ alkenyl group.

According to any embodiments of the invention, the compound of formula (I) is defined in that $R_2$ represents a $C_{1-3}$ alkyl group optionally substituted with a $C_{1-3}$ alkyl carboxylester group, preferably a $C_{1-2}$ alkyl group optionally substituted with a $C_{1-3}$ alkyl carboxylester group, even more preferably, $R_2$ represents a methyl group, an ethyl group, a methyl acetate group (i.e. $CH_2C(O)OMe$), or an ethyl acetate group (i.e. $CH_2C(O)OEt$).

According to any embodiments of the invention, the compound of formula (I) is defined in that $R_1$ represents a linear $C_{3-7}$ alkyl group or a linear $C_{3-7}$ alkenyl group or a linear $C_{3-7}$ alkynyl group and $R_2$ represents a $C_{1-3}$ alkyl group substituted with a $C_{1-3}$ alkyl carboxylester group.

According to any embodiments of the invention, the compound of formula (I) is defined in that $R_1$ represents a linear $C_{4-6}$ alkyl group or a linear $C_{3-7}$ alkenyl group or a linear $C_{3-7}$ alkynyl group and $R_2$ represents a $C_{1-3}$ alkyl group substituted with a $C_{1-3}$ alkyl carboxylester group.

According to any embodiments of the invention, the compound of formula (I) is methyl-3-oxo-2-pentylcyclopentanacetate, methyl-3-oxo-2-(2-pentenyl)-1-cyclopentaneacetate or (Z)-methyl-3-oxo-2-(2-pentenyl)-1-cyclopentaneacetate. Preferably, the compound of formula (I) is methyl-3-oxo-2-pentylcyclopentanacetate.

The first step of the inventive process is subjecting the starting mixture comprising compounds of formula (I) having a weight ratio of the cis-diastereomers to trans-diastereomers equal or lower than 1:1 to the step of ketal formation, preferably to the step of cyclic ketal formation. Thereby it is understood that the compound of formula (I) is subjected to reaction conditions which form a ketal function. A skilled person is aware of several methods to prepare a ketal.

According to a particular embodiment, the weight ratio of the cis-diastereomers to the trans-diastereomers of the starting mixture is less than 40:60, more preferably less than 30:70, more preferably less than 20:80, more preferably less than 15:85 and even more preferably less than 10:90.

Typically, a ketal can be formed by subjecting a ketone, such as the compound of formula (I), to an alkyl monoalcohol, such as $C_{1-3}$ alkyl mono alcohol, or an alkyl diol, such as defined below, in the presence of a catalyst.

According to a particular embodiment, the ketal formation according to step (a) is carried out in the presence of a catalyst being an acid, preferably $H_2SO_4$, pyridium tosylate, $MHSO_4$ wherein M is an alkaline metal, such as sodium or potassium, $Al_2(SO_4)_3$, heterogeneous solid acid, such as resin acid (e.g. Amberlyst), zeolite or clay, alkyl or aryl sulfonic acid, such as methylsulfonic acid or para-toluonesulfonic acid, more preferably $KHSO_4$.

The amount in which the catalyst, preferably the acid, may be employed in the ketal formation step is typically comprised between 0.01 and 10 mol %, relative to the weight of the substrate. In a preferred embodiment, the catalyst, preferably the acid, is used in a concentration comprised between 0.1 to 5 mol %.

According to a particular embodiment, the ketal formation according to step (a) is carried out in the presence of a $C_{1-3}$ alkyl mono alcohol, such as MeOH or EtOH, or an alkyl diol of formula $HO—C(R_4)H—(C(R_4)_2)_n—H(R_4)C—OH$ wherein n is an integer from 0 to 3 and $R_4$, each independently, is a hydrogen or $C_{1-3}$ alkyl group, preferably in the presence of an alkyl diol of formula $HO—C(R_4)H—(C(R_4)_2)_n—H(R_4)C—OH$.

According to a particular embodiment, the ketal formation according to step (a) is carried out in the presence of ethylene glycol, 1,3-propanediol, 2,3-butanediol, 1,2-propanediol, 2,2-dimethyl-1,3-propanediol, 1,2-butanediol, 2-methyl-1,3-propanediol, preferably ethylene glycol, 1,3-propanediol, 2,2-dimethyl-1,3-propanediol, even more preferably ethylene glycol. In other words, the step (a) of the invention process may be a cyclic ketal formation.

The ketal formation according to step (a) may be carried out in the presence or absence of a solvent. When a solvent is required or used for practical reasons, then any solvent current in such reaction type can be used for the purposes of the invention. Particularly, the ketal formation according to step (a) may be carried out in a hydrocarbon solvent, preferably toluene, hexane, cyclohexane or heptane, more preferably toluene or heptane.

The temperature at which the ketal formation according to step (a) can be carried out is comprised between 60° C. and the re fluxing temperature of the solvent, substrate or the alcohol. Preferably, the temperature is in the range of between 60° C. and 180° C., more preferably between 110° C. and 165° C. and even more preferably between 110° and 150° C. A pers on skilled in the art is also able to select the preferred temperature as a function of the melting and boiling point of the starting material and final products as well as of the solvent.

The second step of the inventive process is subjecting the mixture resulting from step (a) to the step of separating the trans-diastereomers and cis-diastereomers. A skilled person is aware of several methods of separating diastereomers. Typically such methods comprise column chromatography, distillation etc.

According to a particular embodiment, the separation according to step (b) is carried out by distillation, preferably by fractionated distillation.

The temperature at which the distillation can be carried out is comprised between 60° C. and 150° C., preferably between 100° C. an d 130° C. A person skilled in the art is also able to select the preferred temperature as a function of the melting and boiling point of the starting material and final products.

The pressure at which the distillation can be carried out is at ambient pressure or under vacuum. Preferably, the pressure at which the distillation can be carried out is comprised between 0.1 mbar to 10 mbar.

The third step of the inventive process is subjecting the cis-diastereomer resulting from step (b) to the step of hydrolyzing the ketal of the cis-diastereomer.

According to a particular embodiment, the hydrolyzing according to step (b) is carried out in the presence of a hydrolyzing agent. A skilled person is aware of several methods to hydrolyze a ketal. Particularly, the hydrolysis may be performed in a presence of an acid. Said acid may be an acid being insoluble in aprotic and apolar solvents and soluble in water with solubility in water of at least 200 g $L^{-1}$. Said acid may process a pKa between 1 and 6.9. Said acid may be citric acid, malic acid, fumaric acid or tartric acid, preferably aqueous citric acid or tartric acid, even more preferably aqueous citric acid.

The amount in which the hydrolyzing agent, preferably the acid, may be employed in the hydrolyzing step is typically comprised between 0.1 and 50 mol %, relative to the weight of the substrate. In a preferred embodiment, the hydrolyzing agent, preferably the acid, is used in a concentration comprised between 5 to 30 mol %.

The hydrolyzing according to step (c) may be carried out in the presence or absence of a solvent. When a solvent is required or used for practical reasons, then any solvent current in such reaction type can be used for the purposes of the invention. Particularly, the hydrolyzing according to step (c) may be carried out neat or in heptane, preferably in heptane.

As an optional additional step, the cis-diastereomers resulting from step (c) can be subjected to a further purification step. A skilled person is aware of several methods of purifying diastereomers. Typically such methods comprise column chromatography, distillation etc. Preferably, the cis-diastereomers resulting from step (c) can be subjected to a further fractionated distillation, even more preferably flash fractionated distillation.

A further aspect of the present invention is a compound according to formula (II)

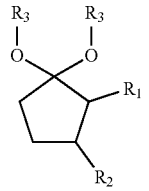

wherein $R_1$ and $R_2$ have the same meaning as the compound according to formula (I), and $R_3$ represent, each independently, a $C_{2-3}$ alkyl group or, when two $R_3$ taken together, is a bivalent group —$C(R_4)H$—$(C(R_4)_2)_n$—$H(R_4)C$— wherein n is an integer from 0 to 3 and $R_4$, each independently, is a hydrogen or $C_{1-3}$ alkyl group, with the proviso that at least one $R_4$ is a linear or branched $C_{1-3}$ alkyl group when n is 0; provided that methyl 2-(3,3-diethoxy-2-propylcyclopentyl)acetate, methyl 2-(2-pentyl-3,3-dipropoxycyclopentyl)acetate, methyl 2-(2-ethyl-6-pentyl-1,4-dioxaspiro[4.4]nonan-7-yl)acetate, methyl 2-(1-pentyl-6,10-dioxaspiro[4.5]decan-2-yl)acetate, methyl 2-(7,9-dimethyl-1-pentyl-6,10-dioxaspiro[4.5]decan-2-yl)acetate, methyl 2-(3,3-diethoxy-2-heptylcyclopentyl)acetate and methyl 2-(3,3-diethoxy-2-hexylcyclopentyl)acetate are excluded.

The invention will now be described in further detail by way of the following examples, wherein the abbreviations have the usual meaning in the art, the temperature is are indicated in degrees centigrade (C).

EXAMPLES

The invention will now be described in further detail by way of the following examples, wherein the abbreviations have the usual meaning in the art, the temperatures are indicated in degrees centigrade (° C.). NMR spectra were acquired using either a Bruker Avance II Ultrashield 400 plus operating at 400 MHz, ($^1$H) and 100 MHz ($^{13}$C) or a Bruker Avance III 500 operating at 500 MHz ($^1$H) and 125 MHz ($^{13}$C) or a Bruker Avance III 600 cryoprobe operating at 600 MHz ($^1$H) and 150 MHz ($^{13}$C). Spectra were internally referenced relative to tetramethyl silane 0.0 ppm. $^1$H NMR signal shifts are expressed in S ppm, coupling constants (J) are expressed in Hz with the following multiplicities: s, singlet; d, doublet; t, triplet; q, quartet; m, multiplet; b, broad (indicating unresolved couplings) and were interpreted using Bruker Topspin software. $^{13}$C NMR data are expressed in chemical shift S ppm and hybridization from DEPT 90 and DEPT 135 experiments, C, quaternary, (s); CH, methine (d); $CH_2$, methylene (t); $CH_3$, methyl (q).

Example 1

The Inventive Process for Methyl-3-oxo-2-pentylcyclopentanacetate 1.1. Ketal Formation Into a 1 L flask, equipped with a mechanical stirrer, a reflux condenser and a Dean Stark apparatus, 250 g of methyl-3-oxo-2-pentylcyclopentanacetate (96.2% purity), 400 g of toluene, 140 g of ethylene glycol and 2.3 g of potassium hydrogen sulfate were added. The resulting mixture is brought to reflux during 10 h while removing water continuously by azeotropic distillation. The reaction is cooled to 50° C., subsequently neutralized by aqueous potassium carbonate and washed with water. After evaporation to dryness, 290 g of a crude material consisting of 20% methyl-3-oxo-2-pentylcyclopentanacetate, 67% trans-methyl-3-oxo-2-pentylcyclopentanacetate ethyleneglycol ketal and 10% cis-methyl-3-oxo-2-pentylcyclopentanacetate ethyleneglycol ketal were obtained.

1.2. Fractional Distillation

A fractional distillation of the crude material was conducted ($T_{vap}$ 92-110° C./1 mbar).

3 main fractions were obtained.

Fraction 1: methyl-3-oxo-2-pentylcyclopentanacetate 43.6 g (97.5% purity)

Fraction 2: trans-methyl-3-oxo-2-pentylcyclopentanacetate ethyleneglycol ketal 199.8 g (99.2% purity; 83.8% yield)

Fraction 3: cis-methyl-3-oxo-2-pentylcyclopentanacetate ethylenglycol ketal 30.9 g (98.5% purity; 12.9% yield)

1.3. Ketal Hydrolysis

Into a flask 1 L, equipped with a mechanical stirrer and a reflux condenser, 52 g of aq. citric acid (25%), 86 g of cis-methyl-3-oxo-2-pentylcyclopentanacetate ethyleneglycol ketal (98.5% purity and cis:trans ratio of 93:7) and 9 g of heptane were added. The biphasic mixture was vigorously stirred at 80° C. over 4 h. Then the stirring was stopped and the phases were allowed to separate. The water phase was discharged and the organic phase was washed twice with water. The organic phase was evaporated to dryness and after cooling down, 73 g of crude methyl-3-oxo-2-pentylcyclopentanacetate with a cis:trans ratio of 88:12 was obtained.

The crude methyl-3-oxo-2-pentylcyclopentanacetate can be further purified by flash distillation at $T_{vap}$ 108° C./1 mbar. By further flash distillation of the crude methyl-3-oxo-2-pentylcyclopentanacetate, 70.8 g of pure methyl-3-oxo-2-pentylcyclopentanacetate with a cis:trans ratio of 85:15 and 97% yield is obtained.

Example 2

Catalyst Screening for the Ketal Formation

A catalyst screening for the ketal formation of methyl-3-oxo-2-pentylcyclopentanacetate has been carried out using the general process parameters as following:

In a reaction flask were added methyl-3-oxo-2-pentylcyclopentanacetate (1 eq.), toluene 200%, ethylene glycol (1.5 eq.) and catalyst 0.1-5 mol %. The mixture was stirred at reflux over 6 h. Water was continuously removed using a Dean Stark equipment.

The yield and selectivity was determined by using GC (db-1 column (10 m×0.1 mm) with a temperature gradient starting at 100° C. for 0.5 min, then moving at 25° C./min to 150° C. and then 80° C./min to 250° C.; trans isomer retention time: 3.22 min and cis isomer retention time: 3.26 min) from the crude reaction mixture.

The results with various catalysts are shown in Table 1.

TABLE 1

Ketal formation with various catalysts

| catalyst | catalyst loading [mol %] | yield (starting material) [%] | yield (ketal) [%] | selectivity [%] |
|---|---|---|---|---|
| para-toluonesulfonic acid | 3 | 21 | 49 | 70 |
| $Al_2(SO_4)_3$ | 3 | 16 | 81 | 97 |

TABLE 1-continued

Ketal formation with various catalysts

| catalyst | catalyst loading [mol %] | yield (starting material) [%] | yield (ketal) [%] | selectivity [%] |
|---|---|---|---|---|
| Zeolite Y CBV760 | 5 | 11 | 85 | 96 |
| $KHSO_4$ | 1.5 | 16 | 81 | 97 |
| $NaHSO_4$ | 1.5 | 48 | 49 | 97 |
| $H_2SO_4$ | 0.1 | 18 | 75 | 93 |
| pyridinium tosylate | 5 | 14 | 80 | 94 |

Example 3

Process of the Invention with Various Compounds of Formula (I)

3.1 Ketal Formation and Distillation—General Protocol

Into a flask, equipped with a mechanical stirrer, a reflux condenser and a Dean Stark apparatus, 1 equivalent of compound of formula (I), 150% w/w of heptane, 2 equivalents of ethylene glycol and 0.015 equivalents of potassium hydrogen sulfate were added. The mixture was brought to reflux during 10 h while removing water continuously by azeotropic distillation. The reaction was cooled to 50° C., neutralized by aqueous potassium carbonate then washed with water. After evaporation to dryness, the corresponding ketal was obtained. Each crude material was subjected to fractional distillation as reported in example 1.2. in order to get pure trans and pure cis ketal isomer. All data are given in the followings

With Compound of Formula (I) being Methyl-3-oxo-2-hexylcyclopentanacetate

The crude material obtained consisted of 9% methyl-3-oxo-2-hexylcyclopentanacetate, 75% trans-methyl-3-oxo-2-hexylcyclopentanacetate ethyleneglycol ketal and 11% cis-methyl-3-oxo-2-hexylcyclopentanacetat ethyleneglycol ketal.

trans-methyl-3-oxo-2-hexylcyclopentanacetate ethyleneglycol ketal (98% purity)

H1-NMR ($CD_2Cl_2$, 600 MHz) δ 0.88 (t, J=6.9 Hz, 3H), 1.1-1.4 (series of m, 10H), 1.5-1.6 (series of m, 2H), 1.6-1.8 (m, 2H), 1.9 (m, 1H), 2.0 (m, 1H), 2.2 (dd, $J_1$=9.4 Hz, $J_2$=14.6 Hz, 1H), 2.5 (dd, $J_1$=5.0 Hz, $J_2$=14.6 Hz, 1H) 3.6 (s, 3H), 3.8-3.9 (m, 4H).

13C-NMR ($CD_2Cl_2$, 125 MHz) δ 14.3 (q), 23.1 (t), 28.4 (t), 28.4 (t), 29.4 (t), 30.2 (d), 32.2 (t), 35.5 (t), 40.1 (d), 40.5 (t), 51.2 (d), 51.6 (q), 64.4 (t), 65.0 (t), 118.3 (s), 173.6 (s).

cis-methyl-3-oxo-2-hexylcyclopentanacetate ethyleneglycol ketal (96% purity)

H1-NMR ($CD_2Cl_2$, 600 MHz) δ 0.88 (t, J=6.9 Hz, 3H), 1.1-1.4 (series of m, 10H), 1.5-1.6 (series of m, 2H), 1.6-1.8 (m, 2H), 1.9 (m, 1H), 2.0 (m, 1H), 2.2 (dd, $J_1$=9.4 Hz, $J_2$=14.6 Hz, 1H), 2.4 (dd, $J_1$=4 Hz, $J_2$=15.5 Hz, 1H) 3.6 (s, 3H), 3.8-4m, 4H).

13C-NMR ($CD_2Cl_2$, 125 MHz) δ 14.3 (q), 23.1 (t), 24.4 (t), 27.6 (t), 28.6 (t), 30.2 (t), 32.2 (t), 34.8 (t), 35.3 (t), 36.2 (d), 49.5 (d), 51.6 (q), 64.5 (t), 65.2 (t), 118.1 (s), 174.3 (s).

With Compound of Formula (I) being Methyl-3-oxo-2-butylcyclopentanacetate

The crude material obtained consisted of 4% methyl-3-oxo-2-butylcyclopentanacetate, 87% trans-methyl-3-oxo-2-butylcyclopentanacetate ethyleneglycol ketal and 8% cis-methyl-3-oxo-2-butylcyclopentanacetate ethyleneglycol ketal.

trans-methyl-3-oxo-2-butylcyclopentanacetate ethyleneglycol ketal (99% purity)

H1-NMR ($CDCl_3$, 600 MHz) δ 0.89 (t, J=7.0 Hz, 3H), 1.1-1.4 (series of m, 6H), 1.5-1.6 (m, 2H), 1.6-1.8 (m, 2H), 1.9 (m, 1H), 2.1 (m, 1H), 2.2 (dd, $J_1$=9.8 Hz, $J_2$=15.0 Hz, 1H), 2.5 (dd, $J_1$=4.9 Hz, $J_2$=15.0 Hz, 1H) 3.6 (s, 3H), 3.8-4.0 (m, 4H).

13C-NMR ($CDCl_3$, 125 MHz) δ 14.1 (q), 23.1 (t), 28.0 (t), 28.8 (t), 30.3 (t), 35.2 (t), 38.6 (d), 40.3 (t), 50.9 (d), 51.4 (q), 64.0 (t), 64.6 (t), 118.0 (s), 173.5 (s).

cis-methyl-3-oxo-2-butylcyclopentanacetate ethyleneglycol ketal (97% purity)

H1-NMR ($CDCl_3$, 600 MHz) δ 0.89 (t, J=6.9 Hz, 3H), 1.1-1.6 (series of m, 7H), 1.6-1.9 (m, 3H), 2.0 (m, 1H), 2.2 (m, 1H), 2.4 (dd, $J_1$=4 Hz, $J_2$=15.5 Hz, 1H), 2.5 (m, 1H), 3.6 (s, 3H), 3.8-4.0 (m, 4H).

13C-NMR ($CDCl_3$, 125 MHz)) δ 14.1 (q), 23.1 (t), 23.6 (t), 27.2 (t), 30.5 (t), 34.4 (t), 35.1 (t), 35.8 (d), 49.2 (d), 51.4 (q), 64.1 (t), 64.8 (t), 117.8 (s), 174.3 (s).

With Compound of Formula (I) Being 3-Methyl-2-pentylcyclopentan-1-one

The crude material obtained consisted of 7% 3-methyl-2-pentylcyclopentan-1-one, 81% trans-7-methyl-6-pentyl-1,4-dioxaspiro[4.4]nonane and 11% cis-7-methyl-6-pentyl-1,4-dioxaspiro[4.4]nonane.

trans-7-methyl-6-pentyl-1,4-dioxaspiro[4.4]nonane (99% purity)

H1-NMR ($CD_2Cl_2$, 600 MHz) δ 0.88 (t, J=6.9 Hz, 3H), 1.0 (d, J=6.2 Hz, 3H), 1.1-1.4 (series of m, 8H), 1.5-2.1 (series of m, 6H), 3.7-4.0 (m, 4H).

13C-NMR ($CD_2Cl_2$, 125 MHz) δ 14.3 (q), 20.8 (q), 23.0 (t), 28.3 (t), 29.0 (t), 31.0 (t), 32.9 (t), 36.2 (t), 38.7 (d), 56.8 (d), 64.6 (t), 64.9 (t), 119.0 (s).

cis-7-methyl-6-pentyl-1,4-dioxaspiro[4.4]nonane (99% purity)

H1-NMR ($CD_2Cl_2$, 600 MHz) δ 0.87 (t, J=6.9 Hz, 3H), 1.1 (d, J=6.5 Hz, 3H), 1.1-2.3 (series of m, 14H), 3.7-4.0 (m, 4H).

13C-NMR ($CD_2Cl_2$, 125 MHz) δ 14.2 (q), 19.9 (q), 22.9 (t), 27.0 (t), 28.2 (t), 30.0 (t), 32.6 (t), 37.4 (d), 38.4 (t), 53.5 (d), 64.2 (t), 65.2 (t), 118.6 (s).

With Compound of Formula (I) Being Ethyl-3-oxo-2-pentylcyclopentanacetate

The crude material obtained consisted of 7% ethyl-3-oxo-2-pentylcyclopentanacetate, 81% trans-ethyl-3-oxo-2-pentylcyclopentanacetate ethyleneglycol ketal and 11% cis-ethyl-3-oxo-2-pentylcyclopentanacetate ethyleneglycol ketal.

trans-ethyl-3-oxo-2-pentylcyclopentanacetate ethyleneglycol ketal (99% purity)

H1-NMR ($CD_2Cl_2$, 600 MHz) δ 0.88 (t, J=6.9 Hz, 3H), 1.2 (t, J=6.9 Hz, 3H), 1.2-1.4 (series of m, 8H), 1.5 (m, 2H), 1.6-1.8 (m, 2H), 1.9 (m, 1H), 2.0 (m, 1H), 2.2 (m, 1H), 2.5 (dd, $J_1$=5.0 Hz, $J_2$=14.6 Hz, 1H) 3.7-3.9 (m, 4H), 4.0 (q, J=7.1 Hz, 2H).

13C-NMR (CD2Cl2, 125 MHz) δ 14.3 (q), 14.5 (q), 23.0 (t), 28.1 (t), 28.3 (t), 29.3 (t), 32.8 (t), 35.5 (t), 40.1 (d), 40.8 (t), 51.2 (d), 60.4 (t), 64.3 (t), 64.9 (t), 118.3 (s), 173.1 (s).

cis-ethyl-3-oxo-2-pentylcyclopentanacetate ethyleneglycol ketal (95% purity)

H1-NMR ($CD_2Cl_2$, 600 MHz) δ 0.88 (t, J=6.9 Hz, 3H), 1.2 (t, J=6.9 Hz, 3H), 1.2-1.4 (series of m, 8H), 1.5 (m, 1H), 1.6-1.8 (m, 3H), 1.9 (m, 1H), 2.2 (m, 1H), 2.3 (dd, $J_1$=5.0 Hz, $J_2$=14.6 Hz, 1H), 2.6 (m, 1H), 3.7-3.9 (m, 4H), 4.1 (q, J=7.1 Hz, 2H).

13C-NMR ($CD_2Cl_2$, 125 MHz) δ 14.3 (q), 14.5 (q) 23.0 (t), 24.3 (t), 26.8 (t), 27.5 (t), 30.2 (t), 35.0 (t), 35.2 (t) 36.2 (d), 49.4 (d), 60.4 (t), 64.5 (t), 65.2 (t), 118.2 (s), 173.8 (s).

With Compound of Formula (I) Being Methyl (Z)-2-(3-oxo-2-(pent-2-en-1-yl)cyclopentyl)acetate The crude material obtained consisted of 7% methyl (Z)-2-(3-oxo-2-(pent-2-en-1-yl)cyclopentyl)acetate, 77% trans-methyl (Z)-2-(3-oxo-2-(pent-2-en-1-yl)cyclopentyl) acetate ethyleneglycol ketal and 8% cis-methyl (Z)-2-(3-oxo-2-(pent-2-en-1-yl)cyclopentyl)acetate ethyleneglycol ketal.

trans-methyl (Z)-2-(3-oxo-2-(pent-2-en-1-yl)cyclopentyl) acetate ethyleneglycol ketal H1-NMR ($CD_2Cl_2$, 600 MHz) δ 0.95 (t, J=7.5 Hz, 3H), 1.27 (m, 1H), 1.6-1.94 (series of m, 4H), 2.06 (m, 4H), 2.2 (m, 2H), 2.56 (dd, J=15 Hz, J=4.8 Hz, 1H), 3.6 (s, 3H), 3.86 (m, 4H), 5.34 (m, 2H).

13C-NMR ($CD_2Cl_2$, 125 MHz) δ 14.3 (q), 20.9 (t), 26.8 (t), 28.6 (t), 35.5 (t), 39.8 (d), 40.3 (t), 51.5 (q), 51.6 (d), 64.6 (t), 65.0 (t), 118.1 (s), 128.2 (d), 132.1 (d), 173.5 (s).

cis-methyl (Z)-2-(3-oxo-2-(pent-2-en-1-yl)cyclopentyl) acetate ethyleneglycol ketal H1-NMR ($CD_2Cl_2$, 600 MHz) δ 0.95 (t, J=7.5 Hz, 3H), 1.4 (m, 1H), 1.5 (sb, 2H), 1.7-1.9 (series of m, 2H), 1.9-2.1 (m, 4H), 2.2 (m, 1H), 2.4 (dd, J=15.0 Hz, J=4.8 Hz, 1H), 2.5 (m, 1H), 3.6 (s, 3H), 3.86 (m, 4H), 5.34 (m, 2H).

13C-NMR ($CD_2Cl_2$, 125 MHz) δ 14.3 (q), 21.1 (t), 22.4 (t), 27.8 (t), 35.1 (t), 35.1 (t), 36.3 (d), 49.6 (d), 51.6 (q), 64.6 (t), 65.2 (t), 118.1 (s), 128.2 (d), 132.3 (d), 174.2 (s).

With Compound of Formula (I) Being Ethyl (Z)-2-(3-oxo-2-(pent-2-en-1-yl)cyclopentyl)acetate The crude material obtained consisted of 10% ethyl (Z)-2-(3-oxo-2-(pent-2-en-1-yl)cyclopentyl)acetate, 80% trans-ethyl (Z)-2-(3-oxo-2-(pent-2-en-1-yl)cyclopentyl)acetate ethyleneglycol ketal and 8% cis-ethyl (Z)-2-(3-oxo-2-(pent-2-en-1-yl)cyclopentyl)acetate ethyleneglycol ketal.

trans-methyl (Z)-2-(3-oxo-2-(pent-2-en-1-yl)cyclopentyl) acetate ethyleneglycol ketal H1-NMR ($CD_2Cl_2$, 600 MHz) δ 0.95 (t, J=7.4 Hz, 3H), 1.22 (t, J=7.1 Hz, 3H), 1.27 (m, 1H), 1.6-1.8 (series of m, 3H), 1.9 (m, 1H), 2.06 (m, 4H), 2.11-2.26 (series of m, 2H), 2.55 (dd, J=15.0 Hz, J=4.5 Hz, 1H), 3.85 (m, 4H), 4.08 (q, J=7.1 Hz, 2H), 5.36 (m, 2H).

13C-NMR ($CD_2Cl_2$, 125 MHz) δ 14.4 (q), 14.5 (q), 20.9 (t), 26.8 (t), 28.3 (t), 35.5 (t), 39.9 (d), 40.6 (t), 51.6 (d), 60.4 (t), 64.5 (t), 65.0 (t), 118.0 (s), 128.3 (d), 132.3 (d), 173.0 (s).

cis-methyl (Z)-2-(3-oxo-2-(pent-2-en-1-yl)cyclopentyl) acetate ethyleneglycol ketal H1-NMR ($CD_2Cl_2$, 600 MHz) δ 0.95 (t, J=7.4 Hz, 3H), 1.22 (t, J=7.1 Hz, 3H), 1.27 (m, 1H), 1.6-2.0 (series of m, 4H), 2.0-2.2 (m, 4H), 2.2-2.4 (series of m, 2H), 2.66 (m, 1H), 3.82 (m, 4H), 4.1 (q, J=7.1 Hz, 2H), 5.36 (m, 2H).

13C-NMR ($CD_2Cl_2$, 125 MHz) δ 14.3 (q), 14.4 (q), 21.0 (t), 25.8 (t), 27.4 (t), 27.6 (t), 38.0 (t), 38.5 (d), 49.6 (d), 60.7 (t), 64.1 (t), 65.3 (t), 118.0 (s), 128.2 (d), 132.2 (d), 173.6 (s).

3.2 Hyrolysis—General Protocol

Into a flask 1 L, equipped with a mechanical stirrer and a reflux condenser, 60% w/w of Citric acid 25% in water, 1 equivalent of pure Cis ketal obtained in step 3.1 and 10% w/w of Heptane were added. The biphasic mixture were vigorously stirred at 80° C. over 4 h. Then the stirring was stopped and the phases were allowed to separate. The water phase was discharged and the organic phase was washed twice with water. The organic phase was evaporated to dryness and after cooling down, the crude was obtained.

The crudes were further purified by flash distillation at $T_{vap}$ 108/1 mbar given:

Cis-methyl-3-oxo-2-hexylcyclopentanacetate

Cis-methyl-3-oxo-2-hexylcyclopentanacetate was obtained with a cis:trans ratio of 95:5 and 97% yield (purity 99%).

H1-NMR ($CDCl_3$, 400 MHz) δ 0.88 (t, J=6.9 Hz, 3H), 1.1-1.5 (sb, 10H), 1.6 (m, 1H), 1.8 (m, 1H), 1.9-2.2 (series of m, 2H), 2.2 (m, 3H), 2.4 (m, 1H), 3.7 (s, 3H). 13C-NMR ($CDCl_3$, 90 MHz) δ 14.1 (q), 22.6 (t), 24.7 (t), 25.7 (t), 27.4 (t) 29.4 (t), 31.6 (t), 33.7 (t), 35.2 (t), 35.7 (d), 51.7 (q), 52.7 (d), 173 (s), 219.3 (s).

Cis-methyl-3-oxo-2-butylcyclopentanacetate

Cis-methyl-3-oxo-2-butylcyclopentanacetate was obtained with a cis:trans ratio of 94:6 and 97% yield (purity 99%).

H1-NMR ($CDCl_3$, 600 MHz) δ 0.89 (t, J=7.0 Hz, 3H), 1.1-1.7 (series of m, 6H), 1.8 (m, 1H), 2.0-2.5 (series of m, 6H), 2.8 (m, 1H), 3.7 (s, 3H). 13C-NMR ($CDCl_3$, 90 MHz) δ 13.9 (q), 22.7 (t), 24.4 (t), 25.6 (t), 29.6 (t), 33.7 (t), 35.1 (t), 35.7 (d), 51.7 (q), 52.7 (d), 173.0 (s), 219.2 (s).

Cis-3-methyl-2-pentylcyclopentan-1-one

Cis-3-methyl-2-pentylcyclopentan-1-one was obtained with a cis:trans ratio of 98:2 and 99% yield (purity 99%).

NMR As reported in Fink, Michael J.; Chem Cat Chem (2013), 5(3), 724-727

Cis-ethyl-3-oxo-2-pentylcyclopentanacetate

Cis-ethyl-3-oxo-2-pentylcyclopentanacetate was obtained with a cis:trans ratio of 96:4 and 97% yield (purity 99%).

H1-NMR ($CDCl_3$, 400 MHz) δ 0.88 (t, J=6.9 Hz, 3H), 1.3 (t, J=7.1 Hz, 3H+m, 7H), 1.6 (m, 1H), 1.8 (m, 1H), 1.9-2.2 (series of m, 2H), 2.2 (m, 3H), 2.4 (dd, $J_1$=5.9 Hz, $J_2$=15.0 Hz, 1H), 2.8 (m, 1H), 4.1 (q, 2H). 13C-NMR ($CDCl_3$, 90 MHz) δ 14.1 (q), 14.2 (q), 24.7 (t), 25.6 (t), 27.4 (t), 29.4 (t) 31.6 (t) 34.0 (t), 35.2 (t), 35.7 (d), 52.7 (d), 60.6 (t), 172.6 (s), 219.4 (s)

Cis-methyl (Z)-2-(3-oxo-2-(pent-2-en-1-yl)cyclopentyl)acetate

Cis-methyl (Z)-2-(3-oxo-2-(pent-2-en-1-yl)cyclopentyl) acetate was obtained with a cis:trans ratio of 93:7 and 96% yield (purity 97%).

H1-NMR ($CDCl_3$, 400 MHz) δ 0.9-1.0 (t, J=7.5 Hz, 3H+m, 2H), 1.8 (m, 1H), 2.0-2.5 (series of m, 8H), 2.85 (m, 1H), 3.7 (s, 3H), 5.34 (m, 1H), 5.45 (m, 1H). 13C-NMR ($CDCl_3$, 100 MHz) δ 14.1 (q), 20.7 (t), 23.0 (t), 25.7 (t), 33.7 (t), 35.3 (t), 35.6 (d), 51.7 (q), 52.7 (d), 125.5 (d), 133.5 (d), 172.9 (s), 218.8 (s).

Cis-ethyl (Z)-2-(3-oxo-2-(pent-2-en-1-yl)cyclopentyl)acetate

Cis-ethyl (Z)-2-(3-oxo-2-(pent-2-en-1-yl)cyclopentyl)acetate was obtained with a cis:trans ratio of 93:7 and 96% yield (purity 97%).

H1-NMR ($CDCl_3$, 600 MHz) δ 0.96 (t, J=7.5 Hz, 3H), 1.27 (t, J=7.1 Hz, 3H+m, 2H), 1.5 (m, 1H), 1.8 (m, 1H), 2.0-2.5 (series of m, 7H), 2.8 (m, 1H), 4.2 (q, J=7.1 Hz, 2H), 5.2 (m, 1H) 5.3 (m, 1H). 13C-NMR ($CDCl_3$, 90 MHz) δ 14.0 (q), 14.2 (q), 20.7 (t), 23.0 (t), 25.6 (t), 34.0 (t), 35.4 (t), 35.6 (d), 52.7 (d), 60.6 (t), 125.5 (d), 133.5 (d), 172.5 (s), 219.0 (s).

Example 4

Diol Screening for the Ketal Formation

A diol screening for the ketal formation of methyl-3-oxo-2-pentylcyclopentanacetate has been carried out using the general process parameters as following:

In a reaction flask were added methyl-3-oxo-2-pentylcyclopentanacetate (1 eq.), toluene 200%, diol (1.5 eq.) and catalyst 0.1-5 mol %. The mixture was stirred at reflux over 6 h. Water was continuously removed using a Dean Stark equipment.

The yield and selectivity was determined by using GC (db-1 column (10 m×0.1 mm) with a temperature gradient starting at 100° C. for 0.5 min, then moving at 25° C./min to 150° C. and then 80° C./min to 250° C.) from the crude reaction mixture.

The results with various diols are shown in Table 2.

TABLE 2

Ketal formation with various diols

| Diol | methyl-3-oxo-2-pentylcyclo-pentanacetate | trans-methyl-3-oxo-2-pentyl-cyclopentanacetate diol ketal | cis-methyl-3-oxo-2-pentyl-cyclopentanacetate diol ketal |
|---|---|---|---|
| Ethylene glycol | 18 | 69 | 10.5 |
| 1,3-propanediol | 22.4 | 61.6 | 9.4 |
| 2,2-dimethyl-1,3-propanediol | 6 | 78 | 12.6 |

The mixture resulting from step a) as displayed in the above table can be treated exactly the same way as described in Example 1.2. and 1.3. Namely, the separation of trans:cis ketal isomers by distillation followed by selective hydrolysis of cis or trans ketal isomer affording enriched to pure cis methyl-3-oxo-2-pentylcyclopentanacetate.

The invention claimed is:

1. A process for the preparation of a mixture of compounds of formula (I)

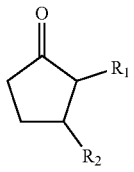

having a weight ratio of the cis-diastereomers to trans-diastereomers higher than 1:1, wherein $R_1$ represents a $C_{1-8}$ alkyl group, a $C_{2-8}$ alkenyl group or a $C_{2-8}$ alkynyl group, each optionally substituted with one or two of a $C_{1-4}$ alkyl alkoxy ether group and/or $C_{1-4}$ alkyl carboxylester group, and $R_2$ represents a $C_{1-6}$ alkyl group, a $C_{2-6}$ alkenyl group or a $C_{2-6}$ alkynyl group, each optionally substituted with an $C_{1-4}$ alkyl alkoxy ether group, a carboxylic acid group or a $C_{1-4}$ alkyl carboxylester group, by subjecting a mixture of compounds of formula (I)

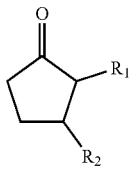

having a weight ratio of the cis-diastereomers to trans-diastereomers equal or lower than 1:1, wherein $R_1$ and $R_2$ have the same meaning as indicated above, to the steps comprising (a) ketal formation, (b) separating the trans-diastereomers and cis-diastereomers and (c) hydrolyzing the ketal of the cis-diastereomers.

2. The process according to claim 1, wherein $R_1$ represents a linear $C_{3-7}$ alkyl group or a linear $C_{3-7}$ alkenyl group or a linear $C_{3-7}$ alkynyl group.

3. The process according to claim 1, wherein $R_2$ represents a $C_{1-3}$ alkyl group optionally substituted with a $C_{1-3}$ alkyl carboxylester group.

4. The process according to claim 1, wherein the compound of formula (I) is methyl-3-oxo-2-pentylcyclopentanacetate, methyl-3-oxo-2-(2-pentenyl)-1-cyclopentaneacetate or (Z)-methyl-3-oxo-2-(2-pentenyl)-1-cyclopentaneacetate.

5. The process according to claim 1, wherein step (b) is carried out by distillation.

6. The process according to claim 1, wherein step (a) is carried out in the presence of an acid.

7. The process according to claim 1, wherein step (a) is carried out in a hydrocarbon solvent.

8. The process according to claim 1, wherein step (a) is carried out in the presence of a diol of formula HO—C($R_4$)H—($C(R_4)_2$)$_n$—H($R_4$)C—OH wherein n is an integer from 0 to 3 and $R_4$, each independently, is a hydrogen or $C_{1-3}$ alkyl group.

9. The process according to claim 1, wherein step (a) is carried out in the presence of ethylene glycol, 1,3-propanediol, 2,3-butanediol, 1,2-propanediol, 2,2-dimethyl-1,3-propanediol, 1,2-butanediol, or 2-methyl-1,3-propanediol.

10. The process according to claim 1, wherein step (c) is carried out in the presence of an acid.

11. The process according to claim 1, wherein step (a) is carried out in the presence of $H_2SO_4$, pyridium tosylate, $MHSO_4$, wherein M is an alkaline metal, $Al_2(SO_4)_3$, heterogeneous solid acid, or alkyl or aryl sulfonic acid.

12. The process according to claim 1, wherein step (a) is carried out in the presence of $KHSO_4$.

13. The process according to claim 1, wherein step (a) is carried out in toluene or heptane.

14. The process according to claim 1, wherein step (a) is carried out in the presence of ethylene glycol.

15. The process according to claim 1, wherein step (c) is carried out in the presence of citric acid.

*16. The process according to claim 1, wherein the weight ratio of the cis-diastereomers to the trans-diastereomers of the mixture of compounds of formula (I) is less than 40:60.*

*17. The process according to claim 1, wherein the weight ratio of the cis-diastereomers to the trans-diastereomers of the prepared mixture after separating the trans-diastereomers and cis-diastereomers is at least 60:40.*

*18. The process according to claim 1, wherein the ketal formation comprises formation of a ketal compound according to formula*

*(II)*

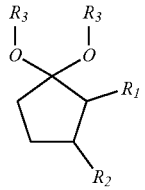

*wherein $R_1$ represents a $C_{1-8}$ alkyl group, a $C_{2-8}$ alkenyl group or a $C_{2-8}$ alkynyl group, each optionally substituted with one or two of a $C_{1-4}$ alkyl alkoxy ether group and/or $C_{1-4}$ alkyl carboxylester group, and $R_2$ represents a $C_{1-6}$ alkyl group, a $C_{2-6}$ alkenyl group or a $C_{2-6}$ alkynyl group, each optionally substituted with an $C_{1-4}$ alkyl alkoxy ether group, a carboxylic acid group or a $C_{1-4}$ alkyl carboxylester group, and*

*$R_3$ represent, each independently, a $C_{2-3}$ alkyl group or, when two $R_3$ taken together, is a bivalent group —C($R_4$)H—($C(R_4)_2$)$_n$—H($R_4$)C— wherein n is an integer from 0 to 3 and $R_4$, each independently, is a hydrogen or $C_{1-3}$ alkyl group, with the proviso that at least one $R_4$ is a linear or branched $C_{1-3}$ alkyl group when n is 0.*

* * * * *